(12) United States Patent
Gerhardt et al.

(10) Patent No.: US 11,033,388 B2
(45) Date of Patent: Jun. 15, 2021

(54) NON-OCCLUSIVE DILATION AND DEPLOYMENT CATHETER DEVICE

(71) Applicant: STRAIT ACCESS TECHNOLOGIES HOLDINGS (PTY) LIMITED, Cape Town (ZA)

(72) Inventors: Thomas Gerhardt, Cape Town (ZA); Peter Rudi Haw, Cape Town (ZA); Jeremy Douglas Jarman, Cape Town (ZA); Giuseppe Geldenhuys, Cape Town (ZA); Kenneth Stuart Park, Cape Town (ZA); Braden Sydney Clive Van Breda, Cape Town (ZA); Edward Charles Mudge, Cape Town (ZA); Deon Bezuidenhout, Cape Town (ZA); Peter Paul Zilla, Cape Town (ZA)

(73) Assignee: Strait Access Technologies Holdings (PTY) Ltd, Cape Town (ZA)

( * ) Notice: Subject to any disclaimer, the term of this patent is extended or adjusted under 35 U.S.C. 154(b) by 222 days.

(21) Appl. No.: 15/571,741

(22) PCT Filed: May 5, 2016

(86) PCT No.: PCT/IB2016/052571
§ 371 (c)(1),
(2) Date: Nov. 3, 2017

(87) PCT Pub. No.: WO2016/178177
PCT Pub. Date: Nov. 10, 2016

(65) Prior Publication Data
US 2018/0153692 A1 Jun. 7, 2018

(30) Foreign Application Priority Data
May 5, 2015 (GB) .................................. 1507640

(51) Int. Cl.
*A61F 2/24* (2006.01)
*A61F 2/01* (2006.01)
(Continued)

(52) U.S. Cl.
CPC ............ *A61F 2/2433* (2013.01); *A61F 2/013* (2013.01); *A61F 2/243* (2013.01); *A61F 2/958* (2013.01);
(Continued)

(58) Field of Classification Search
CPC ............ A61F 2250/0003; A61F 2/2418; A61F 2/2439; A61F 2230/0091; A61F 2/958;
(Continued)

(56) References Cited

U.S. PATENT DOCUMENTS

| 5,308,356 A | 5/1994 | Blackshear, Jr. et al. |
| 5,569,219 A | 10/1996 | Hakki et al. |

(Continued)

FOREIGN PATENT DOCUMENTS

| EP | 2848279 A1 | 3/2015 |
| WO | 92 18195 A1 | 10/1992 |

(Continued)

OTHER PUBLICATIONS

International Search Report for PCT/IB2016/052571, dated Jul. 27, 2016.
(Continued)

*Primary Examiner* — Thomas McEvoy
(74) *Attorney, Agent, or Firm* — Caesar Rivise, PC

(57) ABSTRACT

The invention provides a non-occlusive dilation and deployment catheter device which includes a catheter having a distal end configured for entering a patient and a proximal end for manipulating the device. A distender is provided at or near the distal end which is movable between a collapsed configuration which enables introduction and removal
(Continued)

thereof to and from an operative site in a vessel or other hollow organ of a patient, and an expanded configuration in which the distender assumes a radially expanded condition and defines a flow path therethrough. The distender includes a substantially tubular, radially expandable frame having a plurality of spaced apertures and at least one inflatable tube threaded through the apertures and shaped to extend in a spiral when inflated. The distender is movable to the expanded configuration by inflating the tube, and movable to the collapsed configuration from the expanded configuration by deflating the tube.

20 Claims, 13 Drawing Sheets

(51) Int. Cl.
*A61F 2/958* (2013.01)
*A61M 25/10* (2013.01)
*A61F 2/90* (2013.01)
*A61F 2/95* (2013.01)

(52) U.S. Cl.
CPC ............... *A61M 25/10* (2013.01); *A61F 2/90* (2013.01); *A61F 2/95* (2013.01); *A61F 2230/0034* (2013.01); *A61F 2230/0078* (2013.01); *A61F 2230/0091* (2013.01); *A61F 2250/0003* (2013.01); *A61F 2250/0039* (2013.01)

(58) Field of Classification Search
CPC ......... A61F 2/2433; A61M 2025/1004; A61M 25/1002
See application file for complete search history.

(56) References Cited

U.S. PATENT DOCUMENTS

| | | | |
|---|---|---|---|
| 5,814,064 A * | 9/1998 | Daniel | A61B 17/22031 606/159 |
| 2008/0275485 A1* | 11/2008 | Bonnette | A61F 2/013 606/200 |
| 2012/0245520 A1 | 9/2012 | Kelly et al. | |
| 2014/0277412 A1* | 9/2014 | Bortlein | A61F 2/2427 623/2.11 |
| 2015/0209556 A1* | 7/2015 | Timothy | A61M 25/1029 606/192 |
| 2015/0238315 A1* | 8/2015 | Rabito | A61F 2/2436 623/2.11 |

FOREIGN PATENT DOCUMENTS

| | | |
|---|---|---|
| WO | 93 07929 A1 | 4/1993 |
| WO | 2004 082533 A1 | 9/2004 |
| WO | 2006 086516 A2 | 8/2006 |
| WO | 2014 030078 A1 | 2/2014 |
| WO | 2014 177893 A1 | 11/2014 |

OTHER PUBLICATIONS

English Translation of Office Action dated Jan. 8, 2020 for CN Application No. 201680036808.2.

* cited by examiner

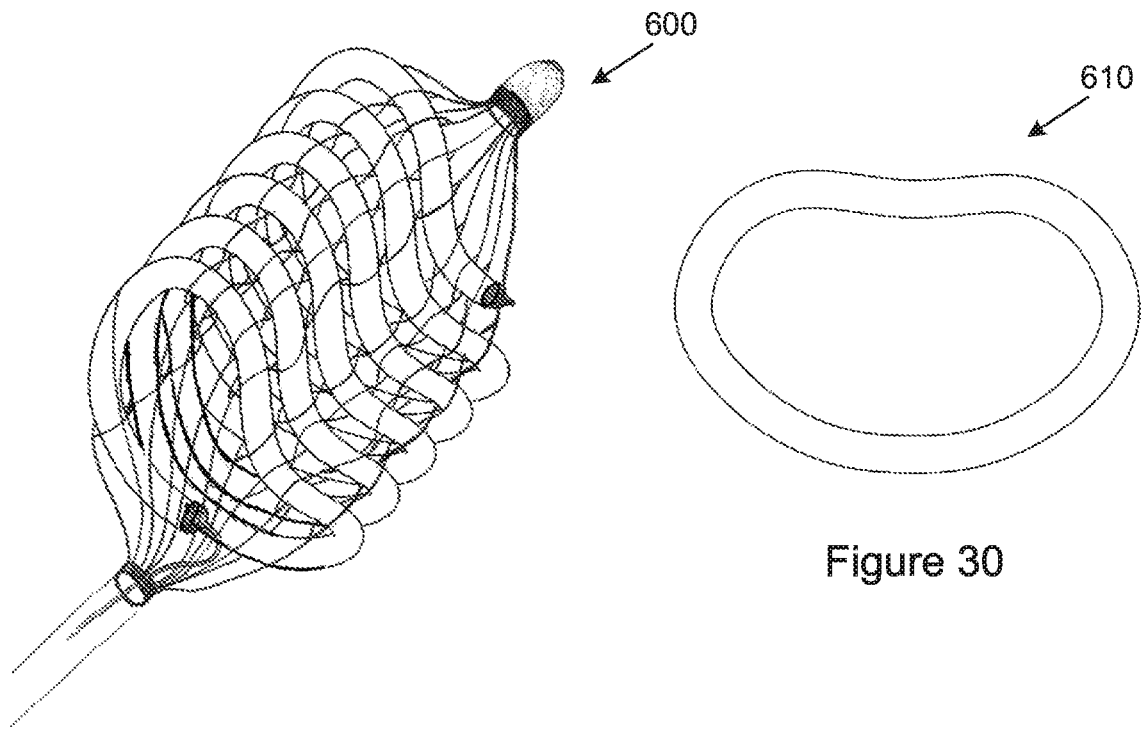
Figure 29
Figure 30
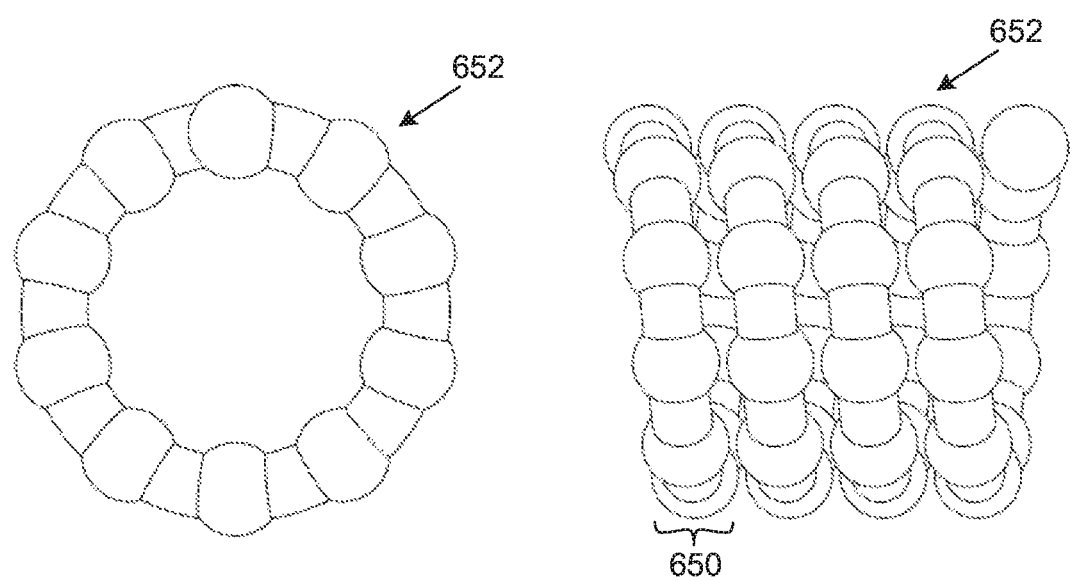
Figure 31A
Figure 31B

NON-OCCLUSIVE DILATION AND DEPLOYMENT CATHETER DEVICE

CROSS-REFERENCE(S) TO RELATED APPLICATIONS

This application claims priority to United Kingdom patent application number 1507640.9 filed on 5 May 2015, which is incorporated by reference herein.

FIELD OF THE INVENTION

This invention relates to medical devices and, more particularly, it relates to medical devices for use in the dilation of blood vessels, the dilation of valves and/or the dilation and/or deployment of structures positioned within blood vessels or the heart.

BACKGROUND TO THE INVENTION

Conventional systems for the dilation of blood vessels, valves or structures, typically stents, positioned in a blood vessel or the heart utilise balloon-like structures or distenders. When such a device is expanded or inflated to perform the dilation, blood flow is occluded through the blood vessel or valve in which the balloon-like distender is used. This occlusion of blood flow may significantly harm the patient, particularly where the dilation is performed on the aortic valve since it prevents the left heart chamber from emptying its contents but also infarction may occur due to a lack of oxygen reaching the tissue during the procedure. Isometric contraction of the heart may lead to the generation of supra-systolic pressures which may lead to overstraining of the heart muscle and, in the case where the distender is used to place a valve, a high risk of valve dislodgement.

In order to overcome the dangers and complications associated with outflow obstruction, highly sophisticated approaches have been developed. To significantly reduce cardiac ejection during the procedure, rapid ventricular pacing may be performed prior to and during inflation of the balloon-like distender. The balloon then needs to be immediately inflated, deflated and withdrawn from the outflow tract. Furthermore, the above procedure may be performed two or three times and must be done within a few seconds thereby further complicating already complex procedures.

In addition, the pacing can sometimes lead to ventricular arrhythmias and should be avoided as far as possible.

In order to permit at least partial blood flow during dilation, helical grooves on the dilation surface have been proposed in EP 0735906. Nevertheless, these will only allow minor perfusion of blood along the outer length of the balloon.

In addition, in order to deploy a stent or to dilate a calcified valve, significant radial force is required. Non-occlusive helical balloons or longitudinal balloons have been proposed in WO2012/099979, however, it is questionable whether these type of balloons are cable of generating sufficient force for stent deployment or dilation of a calcified valve. Furthermore, a problem often exhibited by non-occlusive helical balloons is that they tend to collapse or topple over under high radial loading. This may generally be overcome by stacking the coils of the helix closely together and/or constraining them axially as proposed in WO92/18195, however, this approach requires large amounts of balloon material and may result in unpredictable expansion and collapse thereof. In addition, it may limit radial perfusion and in order to prevent toppling of the helical structure the connection between the coils must be sufficiently robust.

A further problem may arise where the balloon-like structure is expanded in physiological structures having a non-uniform hardness or stiffness, such as calcified lesions within the vasculature. The non-uniform hardness or stiffness may result in localised bulging of the balloon into softer segments thus causing non-circular dilation. In order to overcome this problem, US2012/022563 proposes the inclusion of elongate wire elements which extend along the length of the balloon thereby ensuring uniform circular dilation.

Furthermore, once the dilation procedure has been completed, the balloon must be collapsed to permit removal thereof. Regular pleating and folding of the collapsed balloon is desired, however this is extremely difficult to achieve in a non-occlusive balloon structure.

SUMMARY OF THE INVENTION

In accordance with the invention there is provided a non-occlusive dilation and deployment catheter device which includes
a catheter having a distal end configured for entering a patient and a proximal end for manipulating the device, the device including a distender at or near the distal end of the catheter which is movable between a collapsed configuration which enables introduction and removal thereof to and from an operative site in a vessel or other hollow organ of a patient, and an expanded configuration in which the distender assumes a radially expanded condition and defines a flow path therethrough,
characterised in that the distender includes a substantially tubular, radially expandable frame having a plurality of spaced apertures and at least one inflatable tube threaded through at least some of the apertures, the tube shaped to extend in a spiral when inflated,
and wherein the distender is movable to the expanded configuration by inflating the tube, and movable to the collapsed configuration from the expanded configuration by deflating the tube.

Further features of the invention provide for the frame to have a mesh-like configuration with the tube being threaded through the mesh along a generally spiral path; for the frame to be manufactured from a laser cut tube; alternatively for the frame to be manufactured from a plurality of braided wires; further alternatively for the frame to be manufactured from a plurality of bonded wires or ribbons; still further alternatively for the frame to be manufactured from a sleeve of elastomeric material; and for the frame to be manufactured from any one or more of a shape memory alloy, titanium, stainless steel, cobalt chromium alloys, nickel-cobalt-chromium, tantalum, niobium, platinum iridium, polyether ether ketone (PEEK), polytetrafluoroethylene (PTFE), polyurethane, polyethylene terephthalate (Dacron) or Kevlar® and the like. Elastomeric materials for the sleeve include polyurethanes (PU) (Pellethane, Estane, Texin, Elastane, Carbosil, Elasteon), PU ureas (Biomer, Biospan, Mitrathane, Lycra), carbonate containing PU (Chronoflex, Bionate), Polydimethylsiloxane containing polyurethane/ureas (Pursil, Elasteon, Cardiothane), PUs containing both carbonate and PDMS moeities, or PUs comprising other soft segments (hydrocarbon, dimerol) and or partial crosslinking for improved chemical stability and mechanical properties. Other elastomers include silicone, silastic, silupran, styrene, (co)polyester, polyolefin, polydiene and polyvinyl chloride based synthetic elastomers, or one of the natural rubbers.

In one embodiment of the invention the apertures of the frame are spaced to permit the pitch of successive convolutions of the spiral along the length of the frame to be varied; and for the pitch of the successive convolutions to preferably vary in the range of 1 to 3 times the diameter of the inflatable tube.

In an alternative embodiment of the invention the diameter of the frame varies along its length to permit variation in the outer diameter of the distender along its length in the expanded configuration.

In still a further embodiment of the invention the frame and tube are shaped so that the cross-sectional shape of the distender varies along the length thereof when in the expanded configuration.

In yet a further embodiment of the invention the frame and tube are shaped so that the distender assumes a shape having a non-cylindrical cross-section when in the expanded configuration.

Further features of the invention provide for a valve to be provided within the flow path to permit flow of blood through the flow path predominantly in one direction; for optionally a filter to be secured to be secured to outer surfaces of the distender and the catheter; and for the filter to be manufactured from a sheet of porous material, alternatively to be manufactured from the same material as the frame.

Still further features of the invention provide for the tube diameter to vary along the length thereof; for the tube to be provided with fold lines along the length thereof to facilitate collapsing of the distender; and for the tube to be manufactured from any suitable flexible impervious material including latex, polyurethane, polyolefin, polytetrafluoroethylene (PTFE), fluorinated ethylene propylene (FEP), perfluoroalkoxy (PFA), ethylene tetrafluoroethylene (ETFE), polyether ether ketone (PEEK), polyvinyl chloride (PVC), silicone, Kraton, thermoplastic elastomers such as styrene-ethylene/butylene-styrene (SEBS), (SEBS)-based thermoplastic elastomers, polysiloxane modified SEBS, polymides such as nylons, polyether block amide, polyphenylene sulphides, or polyethylene terephthalate (PET).

Yet further features of the invention provide for collapsing members to be secured to the catheter and outer surfaces of the tube, preferably within the spiral, and which are configured to exert a pulling force onto the tube toward the catheter during collapsing of the distender.

In an embodiment of the invention, the catheter includes an internal member and an external member with the distal end of the frame being attached to the distal end of the internal member and the proximal end of the frame being attached to the distal end of the external member so as to enable the frame to be placed under tension or compression through relative lengthwise movement of the distal ends of the internal member and external member.

In an embodiment of the invention, the catheter includes a biasing member that is attached to one or both of the distal or proximal end of the frame and configured to exert an axial force on the frame so as to place the frame under tension or compression.

Further features of this embodiment provide for the biasing member to be further configured to exert a torsional force on the frame; for the biasing member to be in the form of a spring, alternatively to be in the form of a mesh-like structure capable of exerting an axial and/or torsional force onto the frame; for the biasing member to be attached to the frame externally thereof, alternatively for the biasing member to be internally of the frame; for multiple biasing members to the be attached to the frame; for the biasing member to be integral with the frame, alternatively for the biasing member to be manufactured separate from the frame; and for the biasing member to be manufactured from the same material as the frame, alternatively for the biasing member to be manufactured from a different material.

Further features of the invention provide for the distender to be held in a retractable sheath in the collapsed configuration; and for one or more pressure sensors to be provided on either or both of the catheter and distender.

Still further features of the invention provide for one or more locator arms to be secured to either or both of the frame and the distal end of the catheter and which are deployable from a stowed condition to an operative condition in which they are able to engage with structures at the operative site, preferably to engage with a natural heart valve to locate the distender within the natural heart valve; for the locator arms to be curved in their length and to be flexible with respect to either or both of the frame and catheter; for the locator arms to be hingedly secured to either or both of the frame and the distal end of the catheter; for the locator arms to be manufactured from the same material as the frame, alternatively for the locator arms to be manufactured from an inflatable tube and to be deployable through inflation thereof; and, in the event of the locator arms being inflatable, for the locator arms to have a varying diameter along their length to facilitate folding thereof during collapsing of the distender.

Yet further features of the invention provide for a stent to be pre-crimped over the distender when in a collapsed configuration; and for the stent to support a replacement heart valve or endovascular graft.

BRIEF DESCRIPTION OF THE DRAWINGS

The invention will now be described, by way of example only with reference to the accompanying representations in which:

FIG. 29 is a three-dimensional view of a further embodiment of a non-occlusive dilation and deployment catheter device in accordance with the invention, in which the cross-sectional shape of the distender is non-cylindrical;

FIG. 30 is an exemplary planar view of a mitral valve annulus;

FIGS. 31A and 31B are an end view and a side view respectively of one embodiment of a tube for a distender in accordance with the invention, in which the diameter of the tube varies along the length thereof;

DETAILED DESCRIPTION WITH REFERENCE TO THE DRAWINGS

Figure 1:
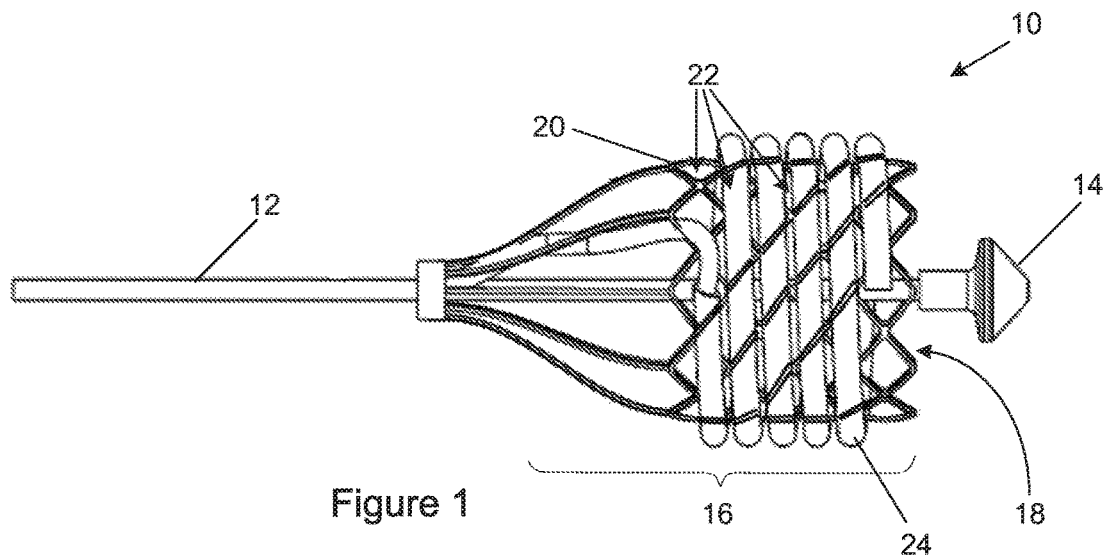
FIG. 1 is a side view of a first embodiment of a non-occlusive dilation and deployment catheter device in accordance with the invention, in which the device is in an expanded condition.
Figure 2:
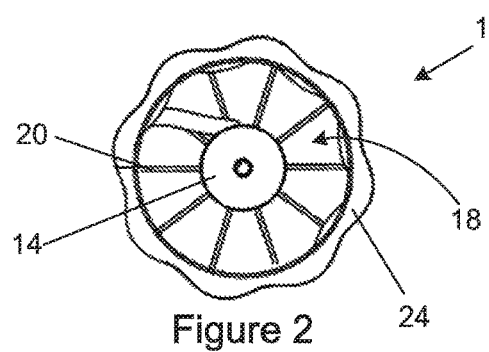
FIG. 2 is an end view of the device shown in FIG. 1.

FIGS. 1 and 2 illustrate a first embodiment of a non-occlusive dilation and deployment catheter device (10) in accordance with the invention. The device (10) includes a catheter (12) having a distal end (14) which is configured for entering a patient and a proximal end (not shown) for manipulating the device (10). The device (10) includes a distender (16) at or near the distal end (14) of the catheter (12) which is movable between a collapsed configuration which enables introduction and removal thereof to and from an operative site in a vessel or other hollow organ of a patient, and an expanded configuration in which the distender (16) assumes a radially expanded condition and defines a flow path (18) therethrough.

The distender (16) includes a substantially tubular, radially expandable frame (20) having a plurality of spaced apertures (22) and at least one inflatable tube (24) threaded through at least some of the apertures (22). The frame (20) has a mesh-like configuration and the tube (24) is threaded through the mesh along a generally spiral path. The lumen of the tube (24) can be inflated, typically by means of a fluid such as a saline solution, but any other suitable fluid can be used. The tube (24) can be manufactured from any suitable flexible impervious material including latex, polyurethane, polyolefin, polytetrafluoroethylene (PTFE), fluorinated ethylene propylene (FEP), perfluoroalkoxy (PFA), ethylene tetrafluoroethylene (ETFE), polyether ether ketone (PEEK), polyvinyl chloride (PVC), silicone, Kraton, thermoplastic elastomers such as styrene-ethylene/butylene-styrene (SEBS), (SEBS)-based thermoplastic elastomers, polysiloxane modified SEBS, polymides such as nylons, polyether block amide, polyphenylene sulphides, or polyethylene terephthalate (PET). In a preferred embodiment the tube is manufactured from polyethylene terephthalate (PET)

Figure 3:
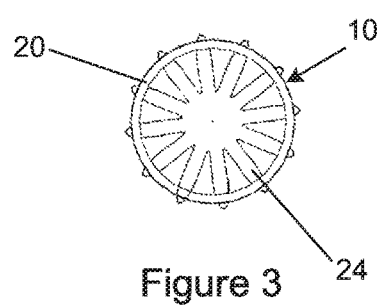
FIG. 3 is an end view of the device shown in FIG. 1, in which the device is in a partially collapsed configuration with the tube deflated.
Figure 4:
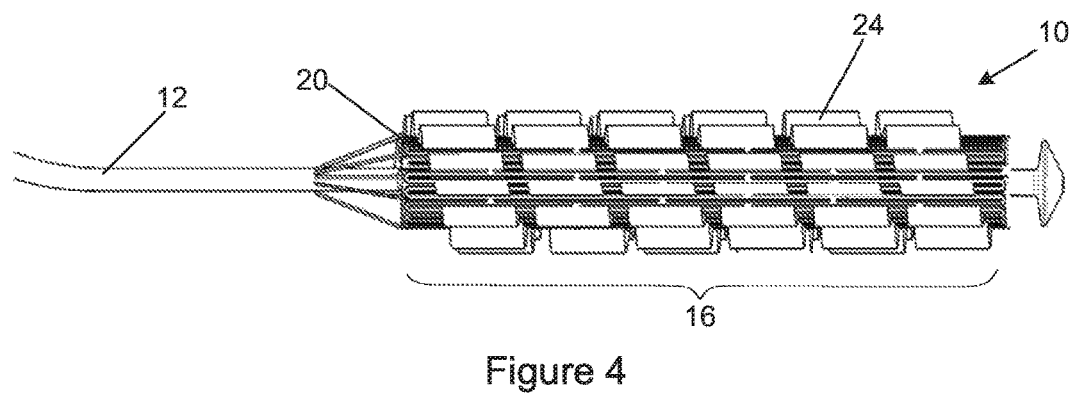
FIG. 4 illustrates a side view of the device of FIG. 1 in a fully collapsed configuration.
Figure 5:
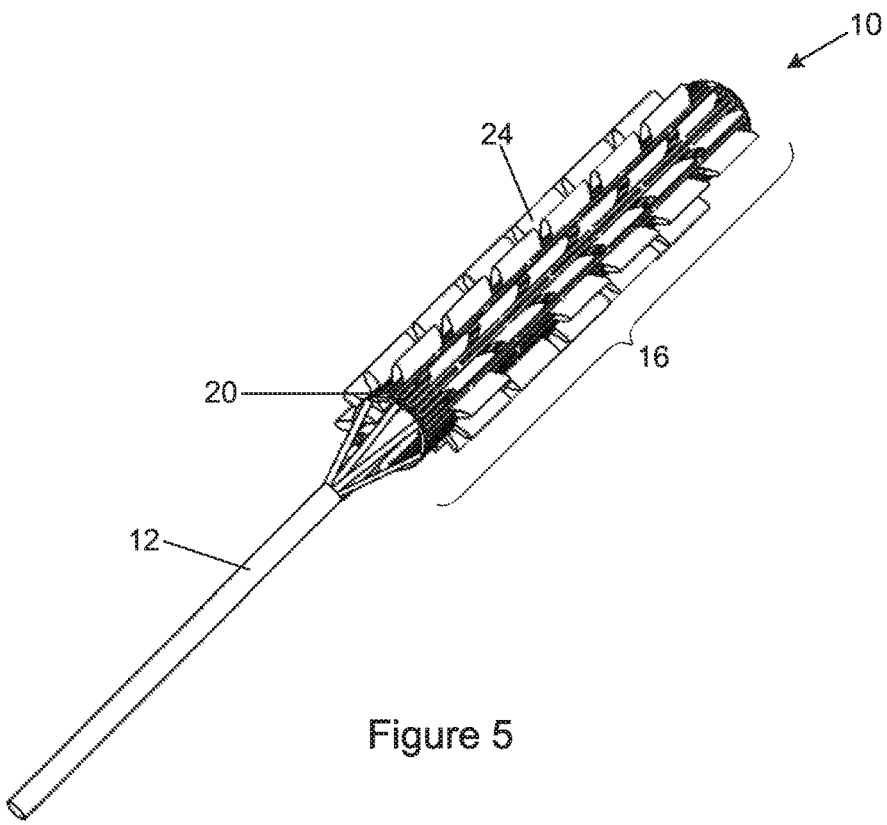
FIG. 5 is a three-dimensional view of the device shown in FIG. 4.

FIGS. 3 to 5 illustrated the device (10) in which the distender (16) is in a collapsed configuration in which the tube (24) is deflated and the frame (20) lies flat against the catheter (12), while FIGS. 1 and 2 illustrate the device (10) in which the distender (16) is in the expanded configuration with the tube (24) inflated and the frame (20) radially expanded. FIG. 3 illustrates the device (10) in which the distender (16) is in a partially collapsed configuration with the tube (24) deflated and neatly pleated.

Figure 6A:
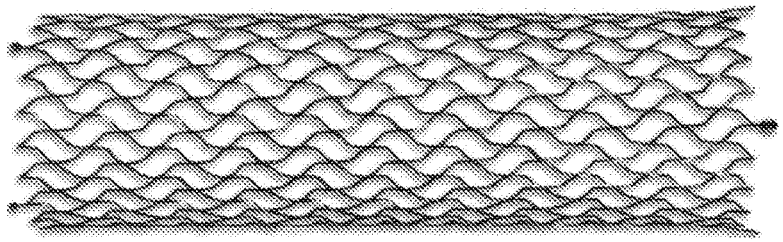
FIG. 6A to 6F illustrate various embodiments of frames having different mesh-type configurations in accordance with the invention.
Figure 6B:
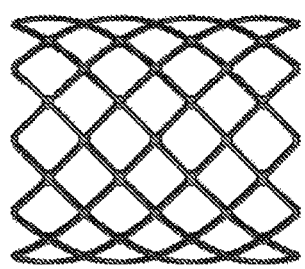
Figure 6C:
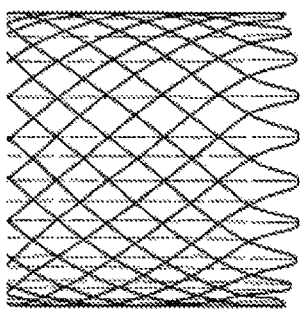
Figure 6D:
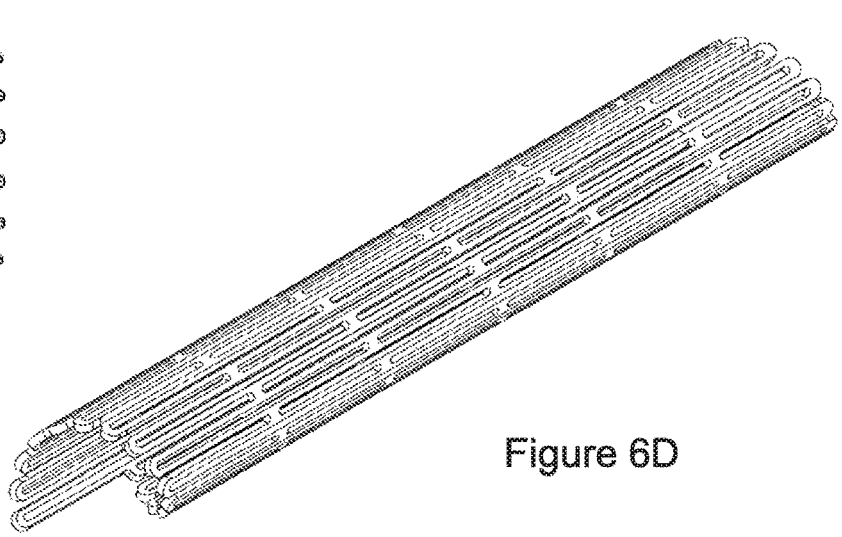
Figure 6E:
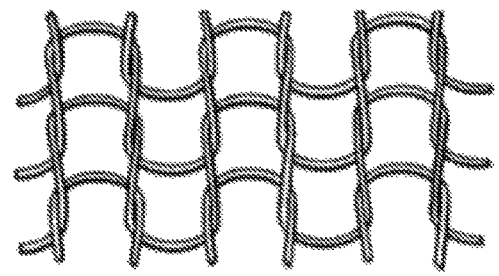
Figure 6F:
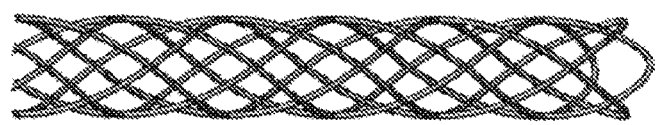

The frame (20) can be manufactured from a laser cut tube using a tube manufactured from titanium, stainless steel, cobalt chromium alloys, nickel-cobalt-chromium, tantalum, niobium, platinum iridium or a shape memory alloy such as nitinol. Alternatively, the frame (20) can also be manufactured from a plurality of bonded wires or ribbons. Yet in a further alternative embodiment, the frame (20) can be manufactured from a plurality of wires that are braided into a mesh-like structure using wires manufactured from one or more of titanium, stainless steel, cobalt chromium alloys, nickel-cobalt-chromium, tantalum, niobium, platinum iridium, polyether ether ketone (PEEK), polytetrafluoroethylene (PTFE), polyurethane, polyethylene terephthalate (Dacron), Kevlar® or a shape memory alloy such as nitinol. FIGS. 6A to 6F illustrate various embodiments of frames having different mesh-type configurations with FIGS. 6A to 6D being manufactured from a laser cut tube, while the frames of FIGS. 6E and 6F are manufactured through weaving or braiding of a plurality of wires. FIG. 6A has a wavy diamond mesh, FIGS. 6B and 6C have a diamond shaped mesh and FIG. 6D a spiral mesh.

It will be appreciated that by manufacturing the frame (20) from a shape memory alloy, such as nitinol, the frame (20) may be set in various configurations as required. For example, by setting the frame (20) with a larger diameter, upon expansion or release thereof, the frame (20) will immediately expand to the pre-set diameter thereby assisting in the expansion of the distender (16) and providing greater resistance to radial forces. The distender (16) may for example be released from a retractable sheath as will be described in more detail further below. Alternatively, if the frame (20) is set to a small diameter, then it will assist in collapsing the distender (16). Yet, if the frame (20) is set to a mid-diameter, then it will assist both in expansion and collapsing of the distender (16).

Figure 7A:
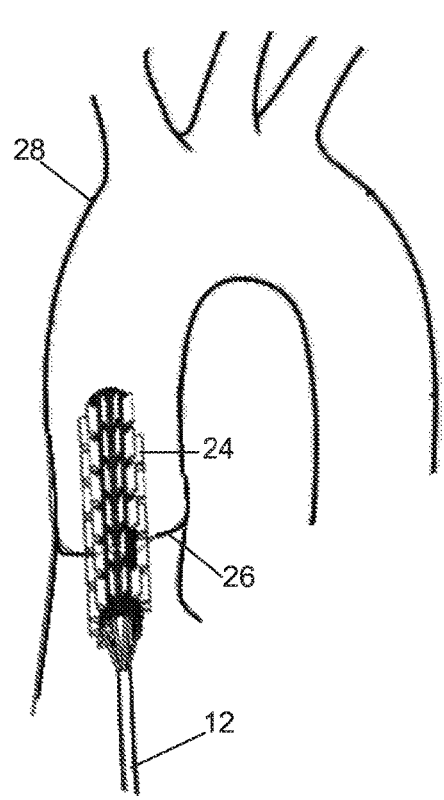
FIG. 7A is a schematic drawing illustrating the device of FIG. 4 being inserted into a valve within the vasculature in its collapsed configuration.
Figure 7B:
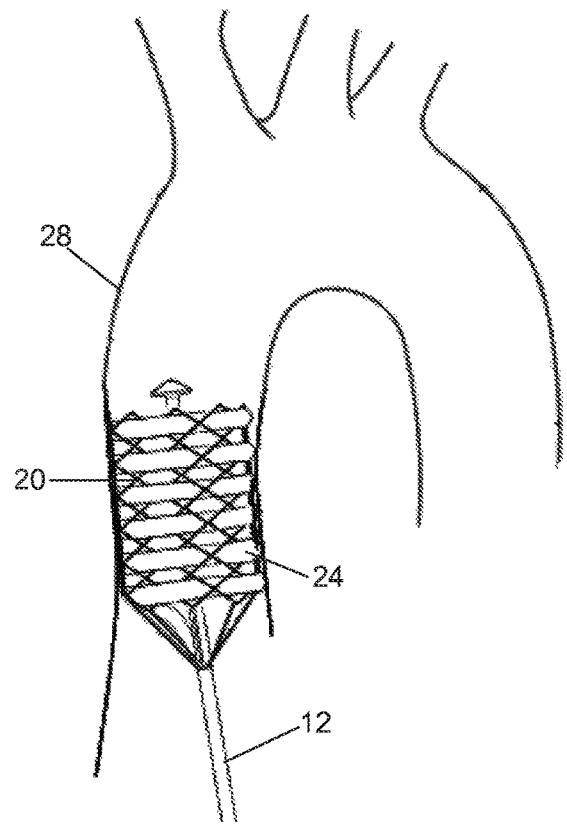
FIG. 7B is a schematic drawing illustrating the device of FIG. 7A in its expanded configuration.

FIGS. 7A and 7B illustrated the device (10) of FIGS. 1 to 5 being inserted into a valve (26) within the vasculature (28) of a patient, in which FIG. 7A illustrates the device (10) in which the distender (16) is in a collapsed configuration enabling navigation thereof to the operative site, in this embodiment the valve (26), and FIG. 7B illustrates the device (10) in which the distender (16) is in the expanded configuration.

In this way the device (10) may be used to dilate a calcified valve, as illustrated in FIGS. 7A and 7B, alternatively, a stent (not shown) supporting a replacement heart valve or endovascular graft can be pre-crimped over the distender (16) when in the collapsed configuration and deployed through movement of the distender (16) from the collapsed configuration to the expanded configuration.

It will be appreciated that since the distender (16) defines a flow path (18) therethrough when in the expanded configuration, blood flow is not interrupted thereby at least to some extent avoiding the detrimental effects generally exhibited by the occlusion of blood flow.

Furthermore, it will be appreciated that the frame (20) will prevent or at least minimise relative movement between adjacent convolutions of the spiral along the length of the distender (16) during inflation or deflation of the tube (24) as well as during radial loading thereof. Further, the frame (20) significantly increases the tube's (24) axial load resistance as well as significantly reduces shear motion of the individual convolutions of the spiral, thereby reducing the tendency to collapse, twist or topple over under radial loading commonly exhibited by helical balloons. Also, providing a frame (20) through which the tube (24) is threaded will increase the axial load resistance without the need for stacking the individual convolutions of the spiral closely together, thereby reducing the amount and/or length of tube (24) required. The frame thus maximises the outward radial force that the spiraled tube or helical balloon can exert. In addition, the frame provides all of the above advantages even where the spirals of the tube are not tightly packed. It has been suggested in the prior art to glue adjacent convolutions of a helical balloon to each other to thereby increase the radial force that the balloon can exert. However, gluing has the consequence that the convolutions are tightly packed together which may be may be unwanted in certain circumstance, for example when radial perfusion of blood is desired.

In addition to the above, the frame (20) will ensure uniform expansion of the tube (24) since the frame (20) causes regular kinking or curving of the tube (24) along the length of the spiral. Also, since the frame (20) causes regular kinking of the tube (24) along the length of the spiral, it will also ensure that any radial forces exerted onto the tube (24) will act about the entire circumference and along the length of the distender (16) rather than having concentrated forces on certain parts of the tube (24). Further, during deflation of the tube (24), the frame (20) will ensure that the tube (24) pleats or folds uniformly due to the regular kinking of the tube (24) along the length of the spiral. Conversely, during deflating of the tube and/or collapsing of the distender, the frame (20) will ensure, at least to a certain extent, that the tube (24) neatly folds or pleats and can thus be returned or withdrawn into the retractable sheath.

Figure 8:
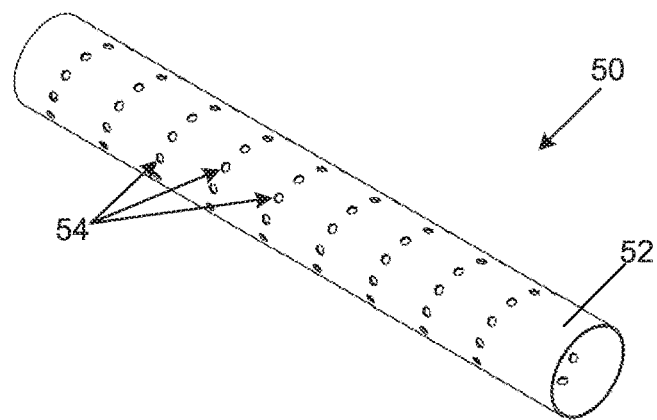
FIG. 8 is a three-dimensional view of an embodiment of a frame in accordance with the invention, in which the frame is manufactured from a sleeve of elastomeric material.
Figure 9:
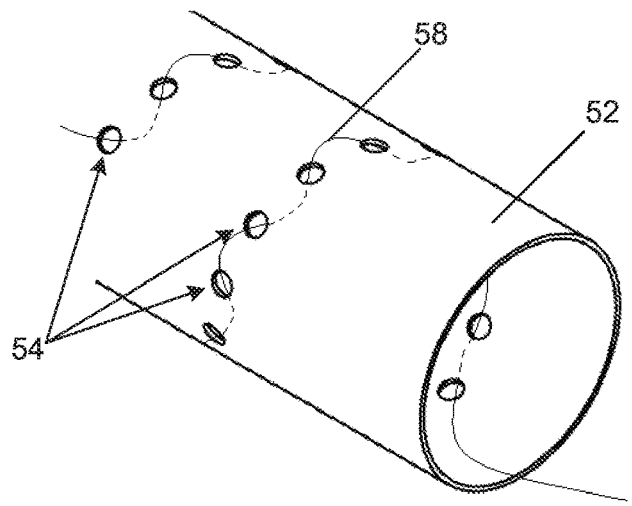
FIG. 9 is a detailed view of the sleeve shown in FIG. 8 illustrating how a tube may be weaved through apertures in the sleeve.
Figure 10:
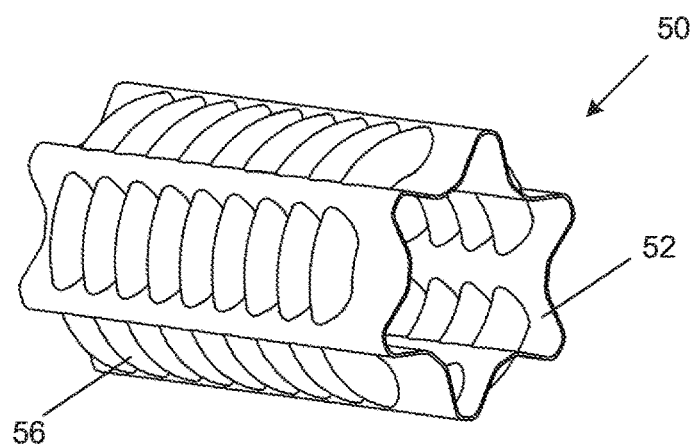
FIG. 10 is a three-dimensional view of an embodiment of a distender in accordance with the invention, in which the frame is manufactured from a sleeve as shown in FIG. 8 in which the distender is in the expanded configuration.

Referring to FIGS. 8 to 10, a further embodiment of a frame (50) is shown in which the frame (50) is manufactured from a sleeve (52) of elastomeric material. The sleeve (52) includes apertures (54) through which the tube (56) may be weaved as indicated by the line (58) in FIG. 9. The apertures (54) are radially spaced about the sleeve (52) in a general spiral path thereby ensuring that the inflated tube (56) adopts a shape in the form of a spiral, as shown in FIG. 10. The sleeve (52) is preferably moulded or extruded in the collapsed condition as shown in FIG. 8, thereby ensuring that the frame (50) may return to the collapsed condition once the tube (56) is deflated.

Elastomeric materials for the sleeve may include polyurethanes (PU) (Pellethane, Estane, Texin, Elastane, Carbosil, Elasteon), PU ureas (Biomer, Biospan, Mitrathane, Lycra), carbonate containing PU (Chronoflex, Bionate), Polydimethylsiloxane containing polyurethane/ureas (Pursil, Elasteon, Cardiothane), PUs containing both carbonate and PDMS moeities, or PUs comprising other soft segments (hydrocarbon, dimerol) and or partial crosslinking for improved chemical stability and mechanical properties. Other elastomers include silicone, silastic, silupran, styrene, (co)polyester, polyolefin, polydiene and polyvinyl chloride based synthetic elastomers, or one of the natural rubbers.

It will be appreciated that since the material of the sleeve (52) will exhibit fairly high frictional contact forces, the weaved tube will be constrained locally through each hole, thereby ensuring minimal tube (56) slippage. Furthermore the sleeve's (52) elasticity permits the apertures (54) therein to deform in such a manner so as to completely accommodate the shape of the inflated tube (56) therein. This allows for an increased contact area between the frame (50) and the tube (56) thereby ultimately reducing the contact stresses and thus reducing the required wall thickness of the inflated tube within it.

The apertures in the sleeve may be circular, oval, elliptic, slit like or the like and are preferably formed when the sleeve is in its collapsed condition which will cause the apertures to have a different shape when the sleeve is in the expanded condition. Designing the apertures in this way may result in both an improved collapsed profile as well as provide optimal constraints on the tube when in the expanded condition. It will be understood that the shape changes in the apertures will be the result of a difference in axial and radial strain during expansion.

Figure 11A:
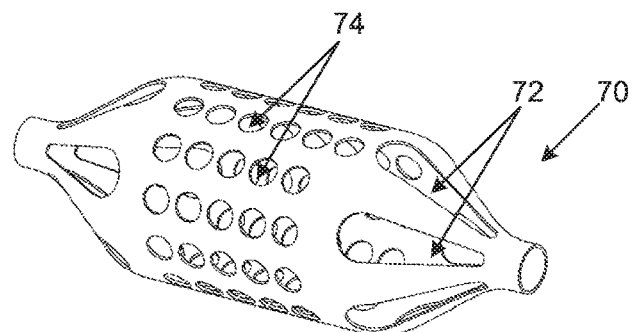
FIG. 11A is a three-dimensional view of an embodiment of a frame in accordance with the invention, in which the frame is manufactured from a sleeve of elastomeric material and may be directly connected to the catheter.

FIG. 11A shows an embodiment of a frame (70) manufactured from an elastomeric material that is similar to the embodiment of the frame (50) shown in FIGS. 8 to 10, provided that in this embodiment the frame (70) may be directly connected to the catheter (not shown). In order to ensure blood perfusion through the frame (70), which may be of particular relevance during certain procedures, longitudinal slits (72) are provided in the region where the frame (70) is connected to the catheter. In addition, and this will be described in more detail further below, by connecting the frame (70) directly to the catheter, a tensional force may be exerted onto the frame (70) which may alter the shape of the apertures (74) in the frame (70) so as to have optimal properties between the frame (70) and the tube. Furthermore and as will be described in greater detail below, the members connecting the frame to the catheter may act as biasing members which may assist in controlling the axial movement of the frame and accordingly the distender during expansion thereof. Also, the members connecting the frame to the catheter may further act as lead ins and outs in order to guide the material of the distender (80) into a retractable sheath as will be described in more detail further below.

Figure 11B:
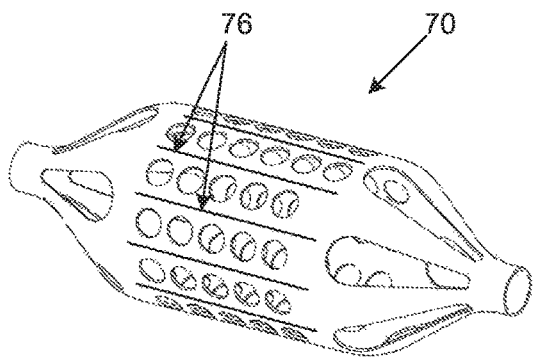
FIG. 11B is a three-dimensional view of the frame shown in FIG. 11A, provided that in this embodiment the frame includes reinforcing members to control axial elongation of the frame.

In addition and as shown in FIG. 11B, reinforcing members (76), preferably noncompliant reinforcing members, may be included in the frame (70) which permit the axial elongation of the frame (70) to be controlled while maintaining radial expansion, during expansion thereof. The reinforcing members (76) may be made from a fibre, such as Kevlar® impregnated into the elastic frame material, or these could be moulded into the frame (70) structure as thickened areas of the same material.

Figure 12:
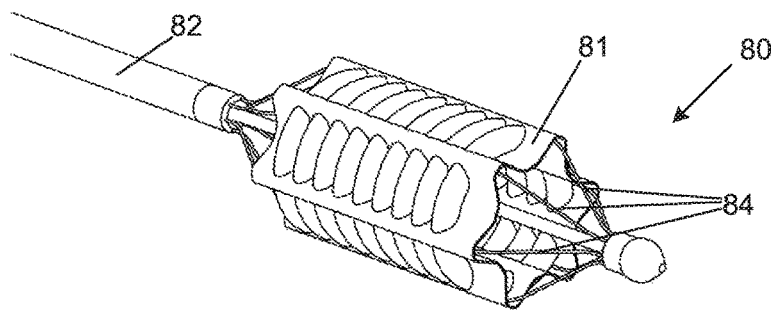
FIG. 12 is a three-dimensional view of an embodiment of a distender in which the frame is manufactured from a sleeve of elastomeric material and which is directly connected to the catheter by means of wires.

FIG. 12 shows a further embodiment of a distender (80) in which the frame (81) is manufactured from an elastomeric material and which is directly connected to the catheter (82) by a plurality of wires (84) that are preferably made from a flexible material. The wires (84) may assist in collapsing the distender (80) as well as provide lead ins and outs in order to guide the material of the distender (80) into a retractable sheath as will be described in more detail further below.

Figure 13:
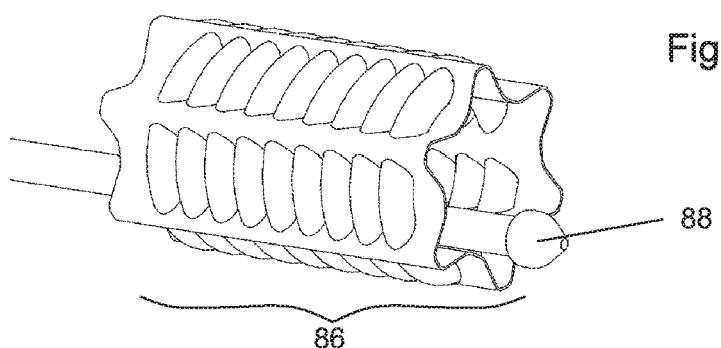
FIG. 13 is a three-dimensional view of a further embodiment of a non-occlusive dilation and deployment catheter device in accordance with the invention, in which the distender is attached to the catheter in a non-centralised way.

It will of course also be appreciated that the distender (86) may also be connected to the catheter (88) in a non-centralised way such that the catheter (88) does not extend centrally through the distender (86), as shown in FIG. 13.

Figure 14:
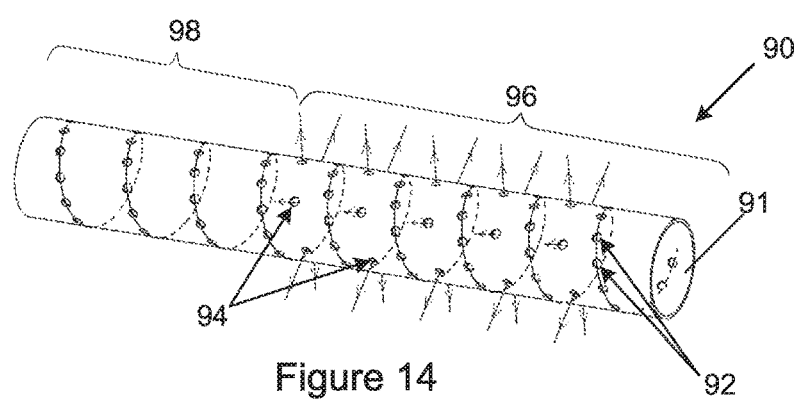
FIG. 14 is a three-dimensional view of an embodiment of a frame manufactured from a sleeve of elastomeric material, in which the additional apertures are provided to permit radial perfusion.

FIG. 14 shows yet a further embodiment of a frame (90) that is manufactured from a sleeve (91) of an elastomeric material. The frame (90) of this embodiment is substantially similar to the frame (50) shown in FIGS. 8 to 10, provided that in this embodiment that frame (90) not only includes apertures (92) through which the tube (not shown) may be woven, but also includes additional apertures (94) that permit radial perfusion. In addition, the additional apertures (94) may only be provided in a first portion (96) of the sleeve (91) while a second potion (98) does not include such additional apertures (94). This may be of particular relevance where the frame (90) is used for an aortic valvuloplasty in which a temporary valve may be provided within the distender, as will be described in more detail further below. In such a case, the first portion (96) may permit radial perfusion through the distender to the aortic annulus in order to feed the coronaries, while the second portion (98) will not permit such radial perfusion below the aortic annulus where such perfusion would simulate a valve with paravalvular leakage.

Figure 15:
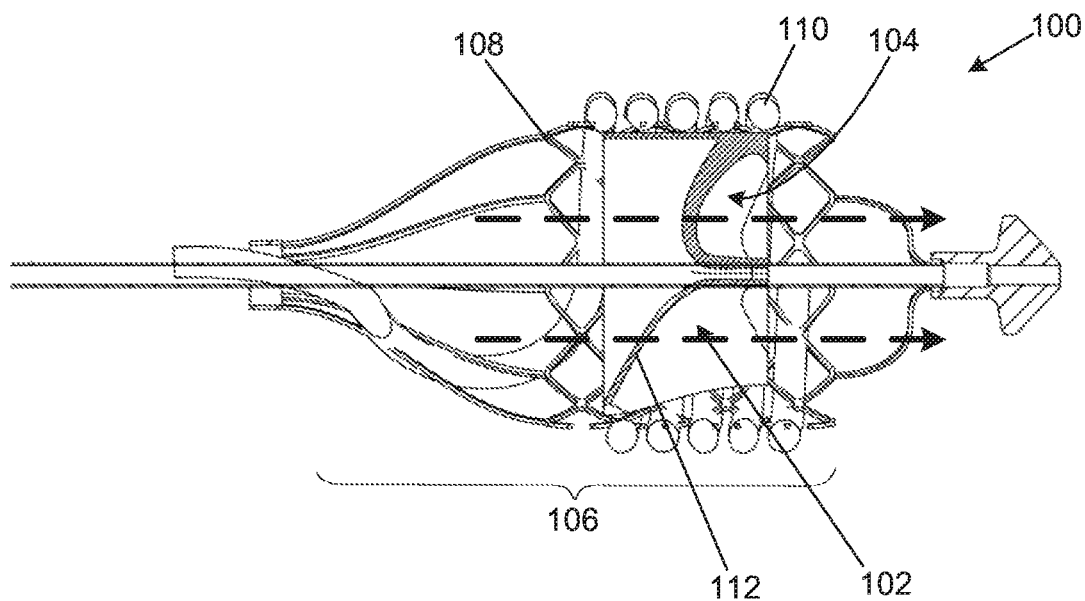
FIG. 15 is a longitudinal section of a second embodiment of a non-occlusive dilation and deployment catheter device in accordance with the invention, in which the device includes a valve.
Figure 16:
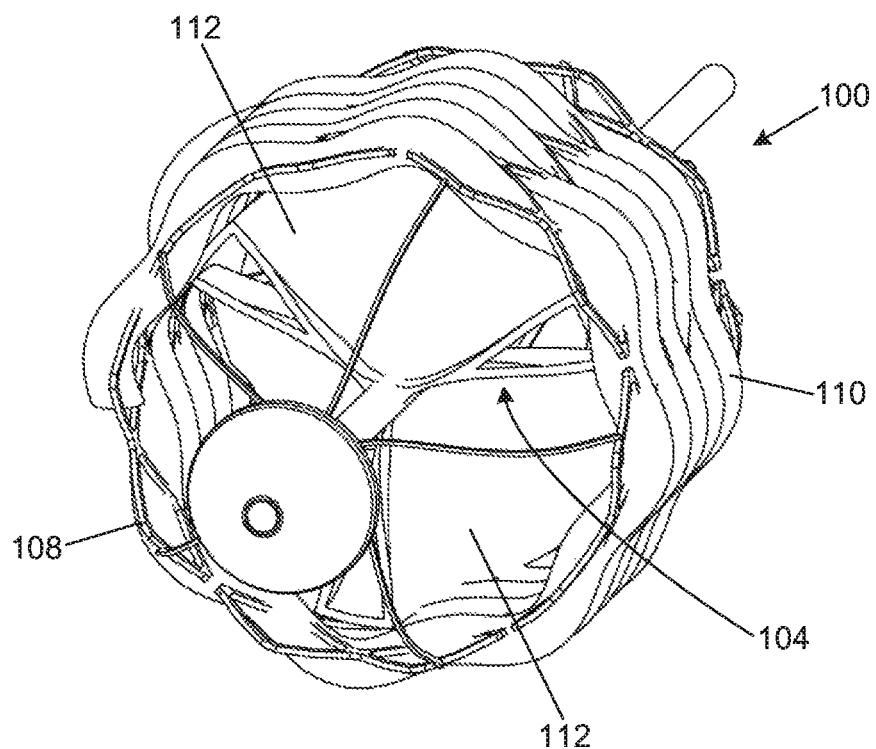
FIG. 16 is a three-dimensional view of the device shown in FIG. 15.

FIGS. 15 and 16 illustrate a further embodiment of a non-occlusive dilation and deployment catheter device (100) in accordance with the invention. The device (100) is substantially similar to the device (10) illustrated in FIGS. 1 to 5, provided that in this embodiment a valve (102) is provided within the flow path (104) defined by the distender (106) so as to permit the flow of blood through the flow path (104) predominantly in one direction, illustrated by the dotted line. The valve (102) is preferably secured to either or both of inner surfaces of the frame (108) and the tube (110) by means of a suitable adhesive. The use of an adhesive provides a tight seal between the valve leaflets (112) and the distender (106) so as to ensure minimisation of paravalvular leakage or leakage of blood around the lines of connection between the valve leaflets (112) and the distender (106) or around the commissures of the valve leaflets.

It will be appreciated that when the distender (106) is in its collapsed configuration, the valve leaflets (112) will lie flat against the catheter. Once the device (100) is manipulated to expand the distender (106) to its expanded configuration the valve (102) will begin to function in the same way as a natural valve and permit blood to flow predominantly in one direction.

Figure 17:
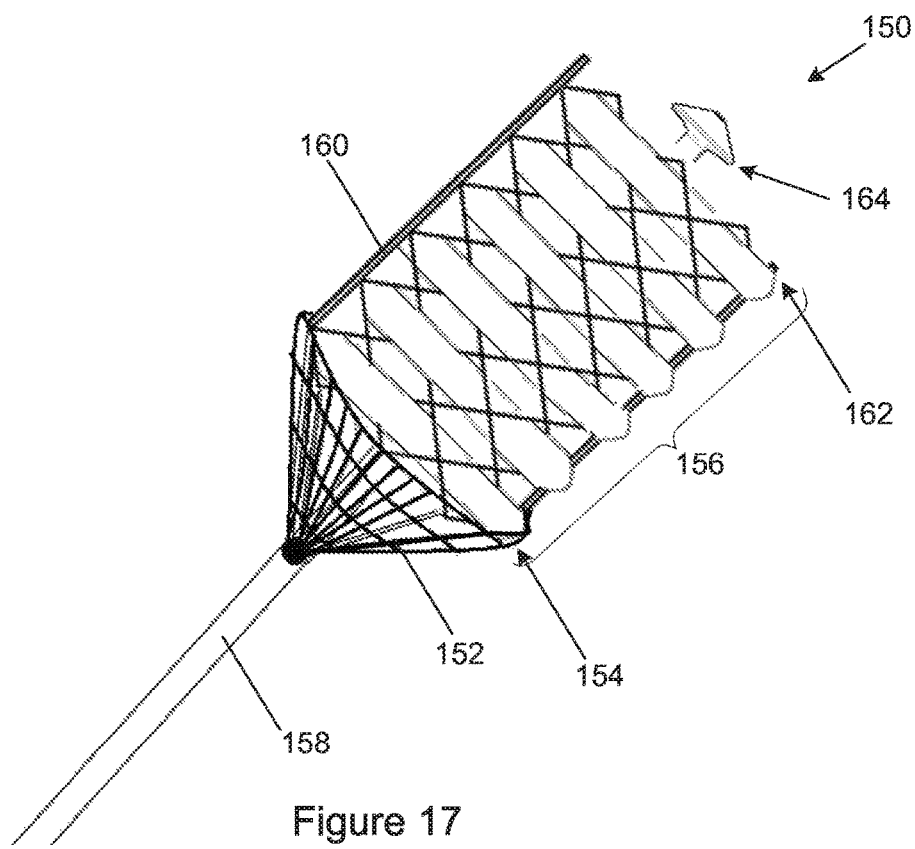
FIG. 17 is a side view of a further embodiment of a non-occlusive dilation and deployment catheter device in accordance with the invention, in which the device includes a filter at the proximal end of the distender.

FIG. 17 illustrates yet a further embodiment of a non-occlusive dilation and deployment catheter device (150) in accordance with the invention. The device (150) is again substantially similar to the device (10) illustrated in FIGS. 1 to 5, provided that in this embodiment a filter (152) is secured at or near the proximal end (154) of the distender (156) and the catheter (158). The filter (152) is manufactured from a suitable porous material and is configured to catch any particles or debris which may be dislodged during expansion of the distender (156). In the embodiment illustrated, the filter (152) is manufactured from the same material as the frame (160), but the filter (152) may of course also be manufactured from a sheet of porous material. In such a case, the material is selected in which its porosity permits blood to freely flow therethrough, but to catch any other particles or debris which may have been dislodged, for example during expansion of the distender (156) in a stenosed vessel.

In addition, in the embodiment illustrated, the filter (152) is attached to the proximal end (154) of the distender (156) but it may also be attached to the distal end (162) of the distender (156) and the distal end (164) of the catheter (158). The position of the filter (152) will typically be selected depending on the approach taken to advance the distender (156) to, for example a valve, thus depending on whether the valve is approached trans-femoral, as illustrated in FIG. 17, or trans-aplical, in which case the filter (152) will be secured to the distal end (162) of the distender (156).

Furthermore, it will be appreciated that since the shape of the filter (152) is generally concave when the distender (156) is in the expanded configuration, and particles or debris will be caught in the filter (152) and remain in the filter (152) even after collapsing of the distender (156) so as to enable removal thereof during removal of the device (150). Also, since the distender (156) may be used in vessels having varying diameters, for example the aortic annulus and the sinuses, then in such a case the distender (156) will expand to a tight fit within the smaller annulus diameter yet sit freely in the larger diameter sinuses. The filter (152) will in such a case be positioned within the larger diameter sinuses and catch any particles or debris which may have been dislodged during expansion of the distender (156).

Figure 18:
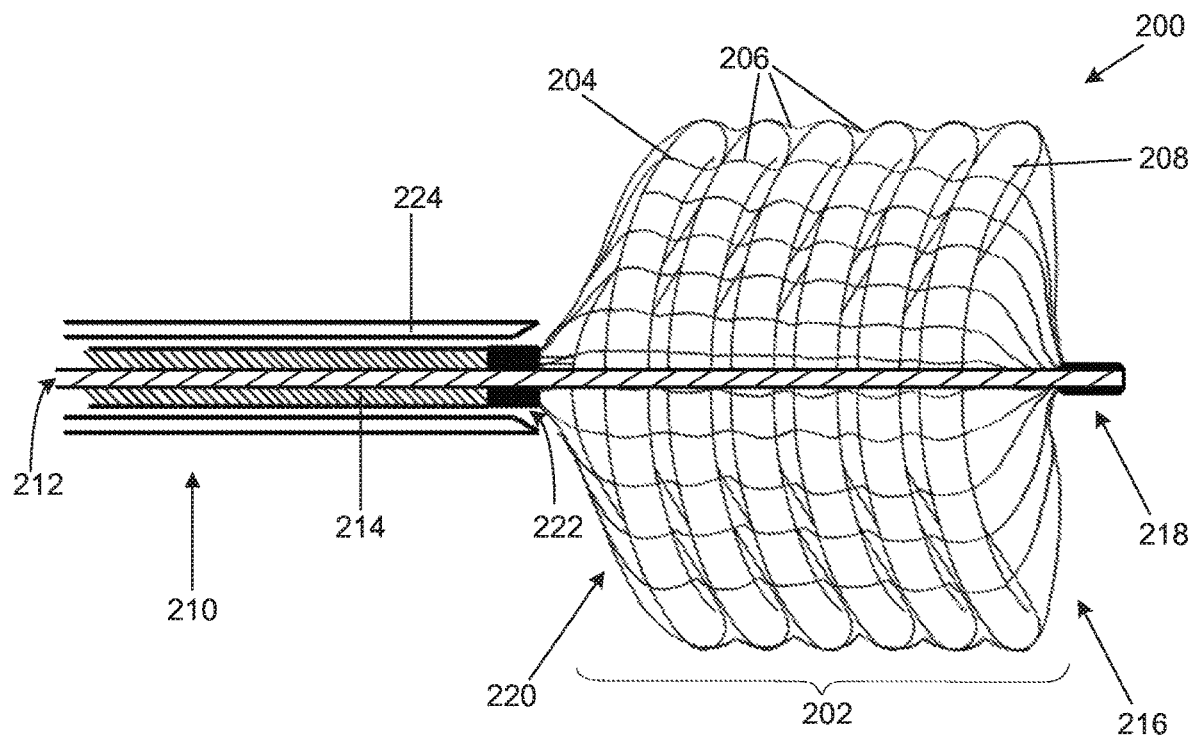
FIG. 18 is a partial longitudinal section of a further embodiment of a non-occlusive dilation and deployment catheter device in accordance with the invention, in which the ends of the frame are secured to the catheter.

FIG. 18 illustrates a further embodiment of a non-occlusive dilation and deployment catheter device (200) in accordance with the invention. In this embodiment, the distender (202) has a frame (204) manufactured from a plurality of wires (206) that are braided into a mesh-like structure with the tube (208) threaded through the mesh in a general spiral path. The catheter (210) includes an internal member (212) which extends internally of an external member (214). The distal end (216) of the frame (204) is attached to the distal end (218) of the internal member (212) while the proximal end (220) of the frame (204) is attached to the distal end (222) of the external member (214). Attachment of the ends (216, 220) of the frame (204) to the internal and external members (212, 214) may be achieved through welding or adhering the wires (206) of the frame (204) to the members (212, 214).

When the distender (202) has been expanded to its expanded configuration, the frame (204) may be placed under tension through lengthwise movement of the distal ends (216, 220) of the members (212, 214) away from each other. Tensioning the frame (204) will minimise relative movement of the individual convolutions of the spiral during expansion and/or radial loading of the distender (202). Furthermore, since the frame (204) is substantially rigid when tensioned, coil shear or toppling of the convolutions during radial loading of the distender (202) is for the most part prevented. It will be appreciated that the frame (70) and distender (80) as shown in FIGS. 11 and 12 respectively may be used in a similar way.

In addition to enabling the frame (204) to be tensioned, attaching of the frame (204) to the distal ends (216, 220) of the members (212, 214) will assist in collapsing the distender (202). During collapsing of the distender (202), the distal ends (216, 220) of the members (212, 214) are simply moved away from each other so that the frame (204) is pulled toward the catheter (210) thereby effectively collapsing the spiral. Furthermore, this will ensure regular pleating of the tube (208) and hence repeatable folding.

Moreover, the device (200) includes a retractable sheath (224) which surrounds at least part of the external member (214). When the device (200) is navigated to the operative site in the vessel or other hollow organ of the patient, the distender (202) is in the collapsed configuration and held within the retractable sheath (224). At or near the operative site, the sheath (224) can then be retracted or withdrawn so as to expose the distender (202) prior to expanding thereof. Once the dilation procedure has been completed the distender (202) can be collapsed, as described above, and the sheath (224) moved forward or over to surround the distender (202) prior to further navigation or removal of the device (200).

It will of course be appreciated that the sheath and/or attachment of the distal and proximal ends of the frame to the catheter may also be used on other embodiments of the invention, such as where the frame is laser cut from a tube of a suitable material or where the frame is manufactured by a plurality of bonded wires or ribbons. Directly attaching the frame to the catheter permits the catheter to be concentric with the inflatable tube and also prevents the tube from snagging on anatomy or other implanted devices during navigation thereof.

In order to further facilitate collapsing of the distender, collapsing members, preferably made from a suitable elastic material, may be secured to the catheter and outer surfaces of the tube, preferably within the spiral and flow path when in the expanded configuration. During expansion of the distender, the collapsing members may then stretch, however, during collapsing of the distender, they act to exert a pulling force onto the tube toward the catheter thereby ensuring quick collapsing of the distender.

Figure 19:
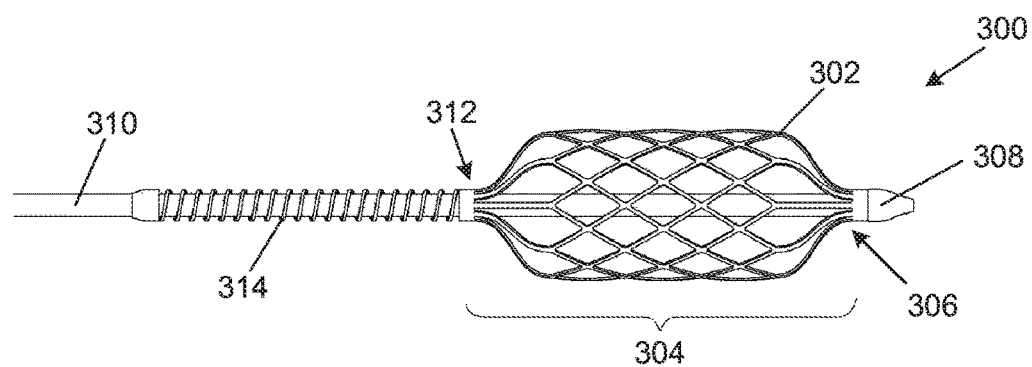
FIG. 19 is a side view of a further embodiment of a non-occlusive dilation and deployment catheter device in accordance with the invention, in which a biasing member in the form of a spring is attached to the proximal end of the frame externally thereof with the frame in the expanded configuration.
Figure 20:
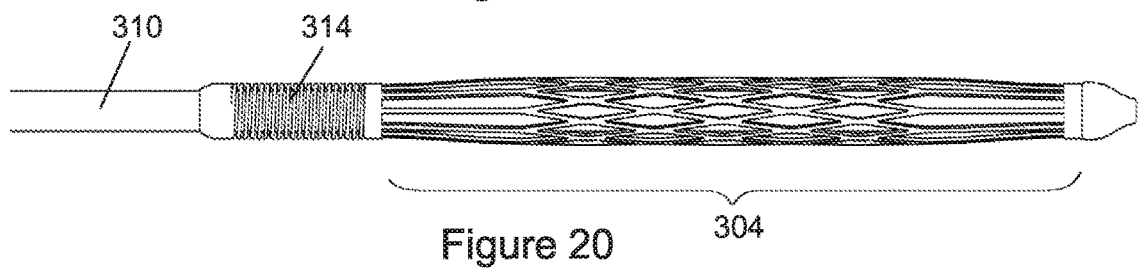
FIG. 20 is a side view of the device shown in FIG. 19 in which the frame is in the collapsed configuration.

FIGS. 19 and 20 show a further embodiment of a non-occlusive dilation and deployment catheter device (300) in accordance with the invention. For clarity purposes only the frame (302) of the distender (304) are shown without the inflatable tube. Similar to the embodiment shown in FIG. 18, in this embodiment, the distal end (306) of the frame (302) is attached to the distal end (308) of the catheter (310) while the proximal end (312) of the frame (302) is attached to a biasing member (314), in this embodiment in the form of a spring that is wound about the catheter (310). Of course other suitable biasing members may also be used. The spring (314) is configured to exert an axial force onto the frame (302) so as to place the frame (302) under tension or compression.

Different to the embodiment shown in FIG. 18, the inclusion of the biasing member (314) permits the frame (302) to be directly attached to the catheter (310) since the biasing member (314) will compensate for the shortening or lengthening of the frame during expansion and collapsing of the distender (304). Furthermore, during compression of the distender (304), the biasing member (314) exerts a tension or pulling force onto the proximal end (312) of the frame (302) thereby lengthening it which may reduce the diameter of the distender (304) and thereby reduce its cross-sectional area when in the compressed configuration.

The biasing member (314) may be manufactured integral with the frame (302) or it may be manufactured separately therefrom and attached to the frame (302) during assembly of the device (300). Furthermore, when manufactured separately, the biasing member may be manufactured from a different material having more suitable properties, for example a medically approved elastic metal or a polymeric material.

Figure 21:
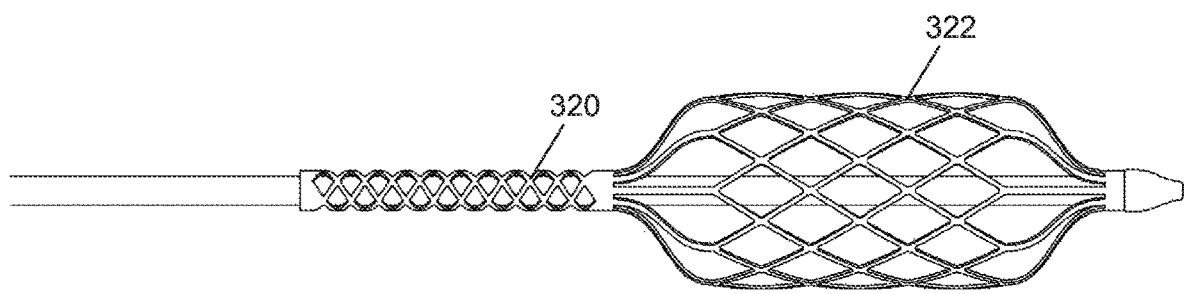
FIG. 21 is a side view of a further embodiment of a non-occlusive dilation and deployment catheter device in accordance with the invention, in which a biasing member is in the form of a mesh-like structure.

It will be appreciated that the biasing member (320) does not have to be in the form of a spring and may also, as shown in FIG. 21, be in the form of a mesh-like structure capable of exerting a desired force onto the frame (322). Furthermore, the biasing member (320) may further be configured to not only exert an axial force but also a torsional force onto the frame (322). The addition of a torsional force may further assist in reducing the collapsed diameter of the frame (322) by twisting the frame (322) during collapsing thereof. In the embodiment illustrated, the mesh-like structure is integrally manufactured with the frame (322) but it may of course also be manufactured separately and then later attached thereto.

Figure 22:
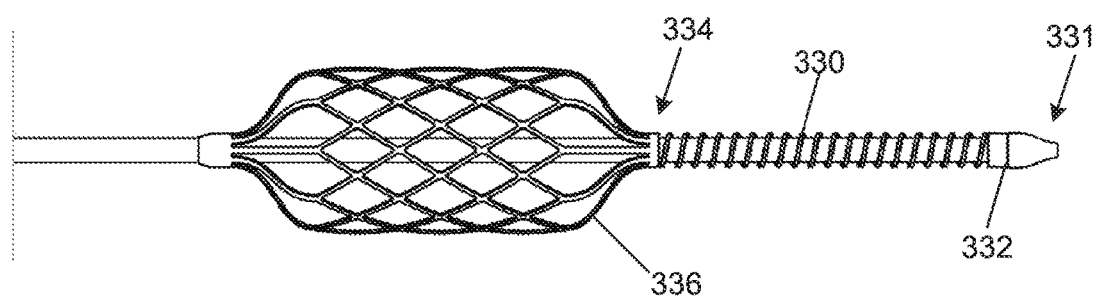
FIG. 22 is a side view of a further embodiment of a non-occlusive dilation and deployment catheter device in accordance with the invention, in which a biasing member in the form of a spring is attached to the distal end of the frame externally thereof.
Figure 23:
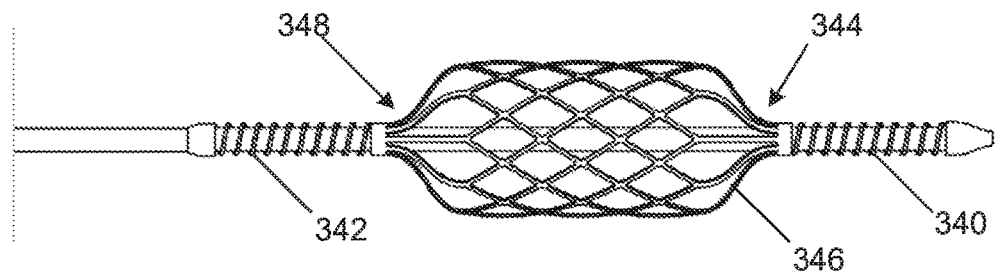
FIG. 23 is a side view of a further embodiment of a non-occlusive dilation and deployment catheter device in accordance with the invention, in which a biasing member is attached to each end of the frame externally thereof.

Instead of attaching the biasing member (314, 320) to the proximal end (312) of the frame (302, 322), the biasing member (330) may of course also be attached to the distal end (331) of the catheter (332) and the distal end (334) of the frame (336), as shown in FIG. 22. Alternatively, and as shown in FIG. 23, multiple biasing members (340, 342), in this embodiment two, may be used with one attached to the distal end (344) of the frame (346) and the other to the proximal end (348) of the frame (346). It will be appreciated that this will ensure that the centre or reference point of the expanded distender remains axially constant since the biasing members on either side will expand equally. This will be of particular relevance when not only positioning is important, but when relative motion of the device is to be kept to a minimum so as to prevent coming in contact with the surrounding anatomy and possibly dislodging calcified debris or implanted devices.

Figure 24:
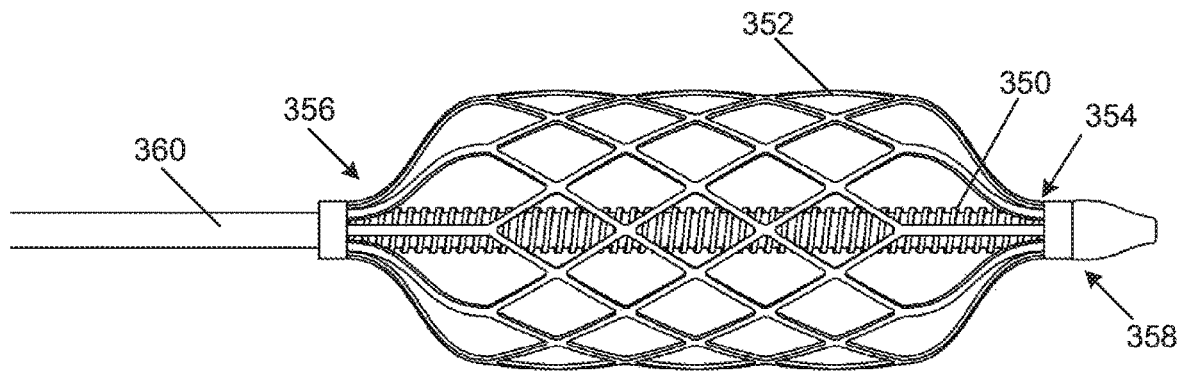
FIG. 24 is a side view of a further embodiment of a non-occlusive dilation and deployment catheter device in accordance with the invention, in which a biasing member is attached internally of the frame.

In still a further embodiment and as shown in FIG. 24, the biasing member (350) may also be internally of the frame (352) and attached to both the distal end (354) as well as the proximal end (356). It will be appreciated that the distal end (354) of the frame (352) may be attached to the distal end (358) of the catheter (360) or separate therefrom so that the proximal end (356) of the frame (352) is able to move along the catheter (360) relative to the distal end (354) of the frame (352).

Figure 25:
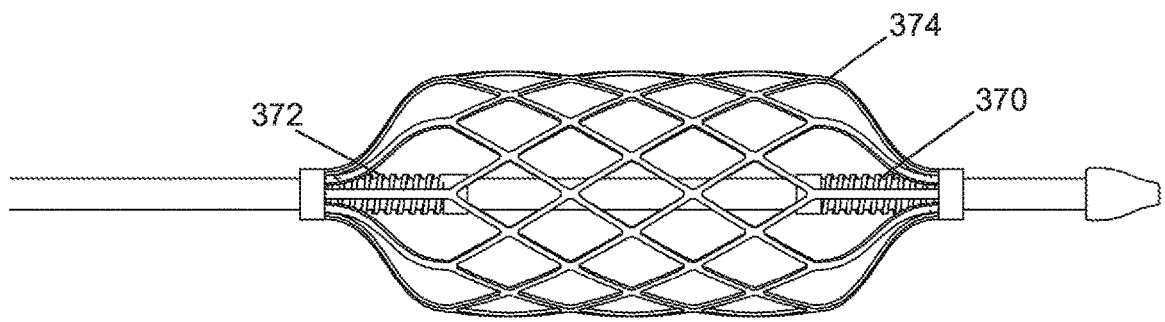
FIG. 25 is a side view of a further embodiment of a non-occlusive dilation and deployment catheter device in accordance with the invention, in which two biasing member are attached internally of the frame, one to each end of the frame.

Alternatively, and as shown in FIG. 25, two separate biasing members (370, 372) may be used that are both internally of the frame (374). It will be appreciated that in this embodiment, the central portion of the frame (374) and accordingly the central portion of the distender remains axially stationary with respect to the catheter. This allows for more accurate positioning and possibly reduced risk of dislodgement of calcium or other implanted devices.

Figure 26A:
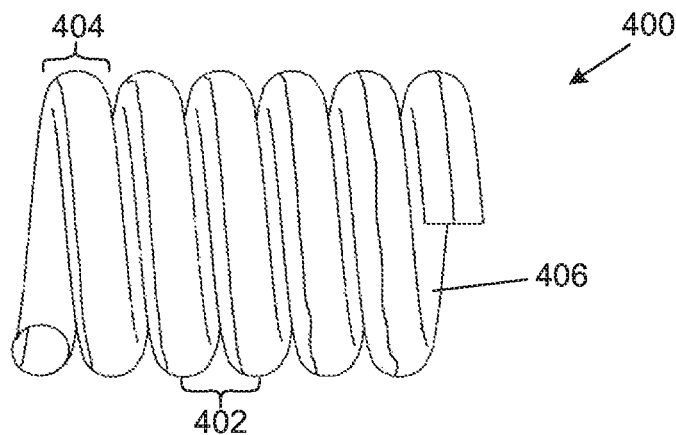
FIG. 26A to 26C are side views of three embodiments of tubes for use in distenders in accordance with the invention, in which the pitch between the individual convolutions of the spiral varies.
Figure 26B:
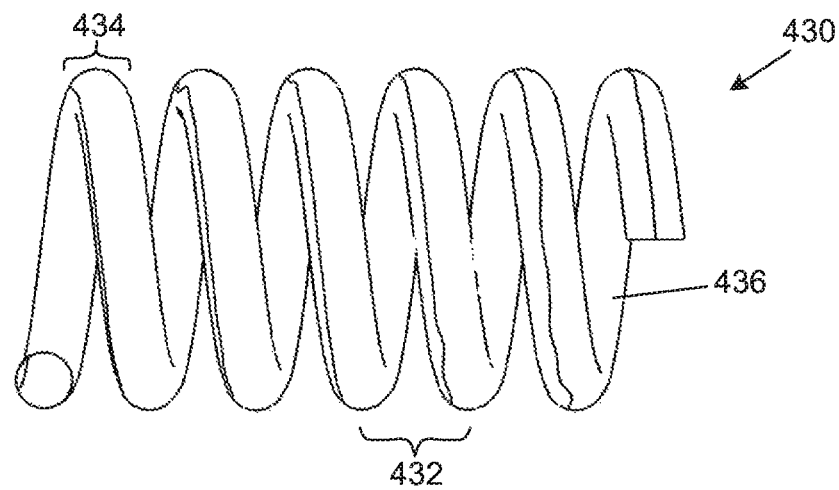
Figure 26C:
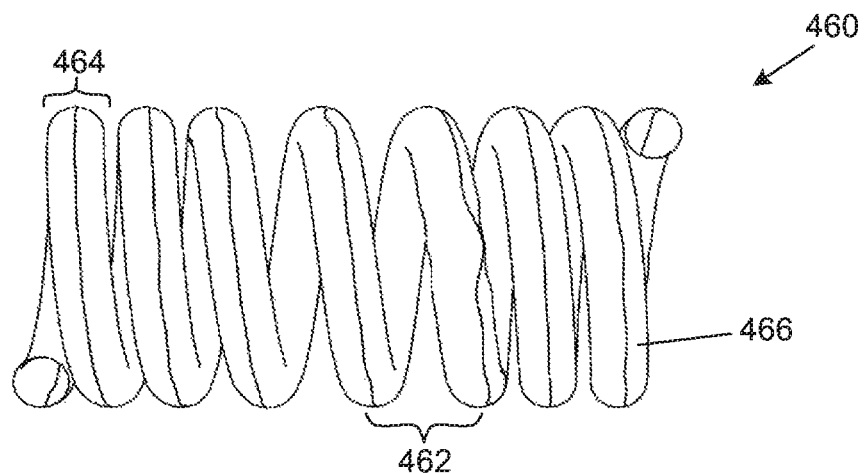

FIGS. 26A to 26C illustrated three embodiments of tubes (400, 430, 460) in accordance with the invention. Since the tube is threaded through at least some of the apertures of the frame, this enables varying the pitch (402, 432, 462) of the successive convolutions (404, 434, 464) of the spiral (406, 436, 466) along the length of the frame. The pitch (402, 432, 462) may be varied as desired, however, it is preferably kept within the range of 1 to 3 times the tube diameter so as to ensure that the distender is capable of effectively expanding and resisting any radial forces exerted thereon without toppling. Furthermore, by permitting the pitch (402, 432, 462) to be varied, the amount of tube (400, 430, 460) required for the distender may be reduced, thus reducing the diameter into which the distender can be collapsed. Also, variation in pitch along the length of the distender will permit perfusion at specific points along the length of the distender which has direct application for coronary perfusion during valvular therapy as well as accurate or at least containable drug delivery.

In addition, the tube may be non-compliant, semi-compliant or compliant. Compliance is a term used for such medical devices to describe the change in diameter of the tube as a function of pressure. Low pressure compliant tubes are typically formed from elastomers such as latex, polyurethane and other thermoplastic elastomers. A low pressure compliant tube may expand by 100 percent or greater upon inflation. Alternatively, high pressure non-compliant tubes expand very little, if at all, upon inflation from a nominal diameter to a rated burst pressure. The rated burst pressure being the maximum pressure at which there is statistical 95 percent confidence level that 99.9 percent of the population of tubes will not burst. As such, high pressure, non-compliant tubes may have a rated burst pressure of up to 20 atmospheres or higher. These type of tubes are generally formed from relatively inelastic materials such as oriented highly crystalline polyethylene terephthalate (PET) films. These type of tubes may have thin walls having high burst pressures. On the other hand, a semi-compliant tube exhibits a moderate degree of expansion when pressurised from its operating pressure, i.e. the pressure at which it reaches its nominal diameter, to its rated burst pressure. The use of semi-compliant and non-compliant tubes will allow the distender to expand to a specific diameter based on the pressure with the tube. This is particularly useful for valve sizing, correct seating in non-circular vasculature or the like.

Figure 27:
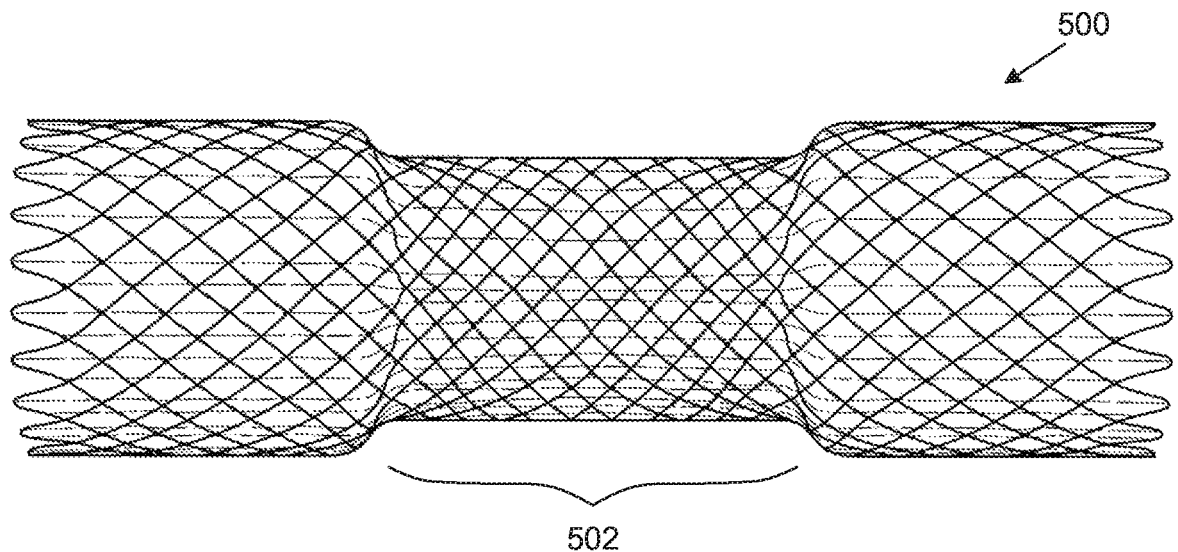
FIG. 27 is a side view of one embodiment of a frame in accordance with the invention, in which the diameter of the frame varies along the length thereof.
Figure 28:
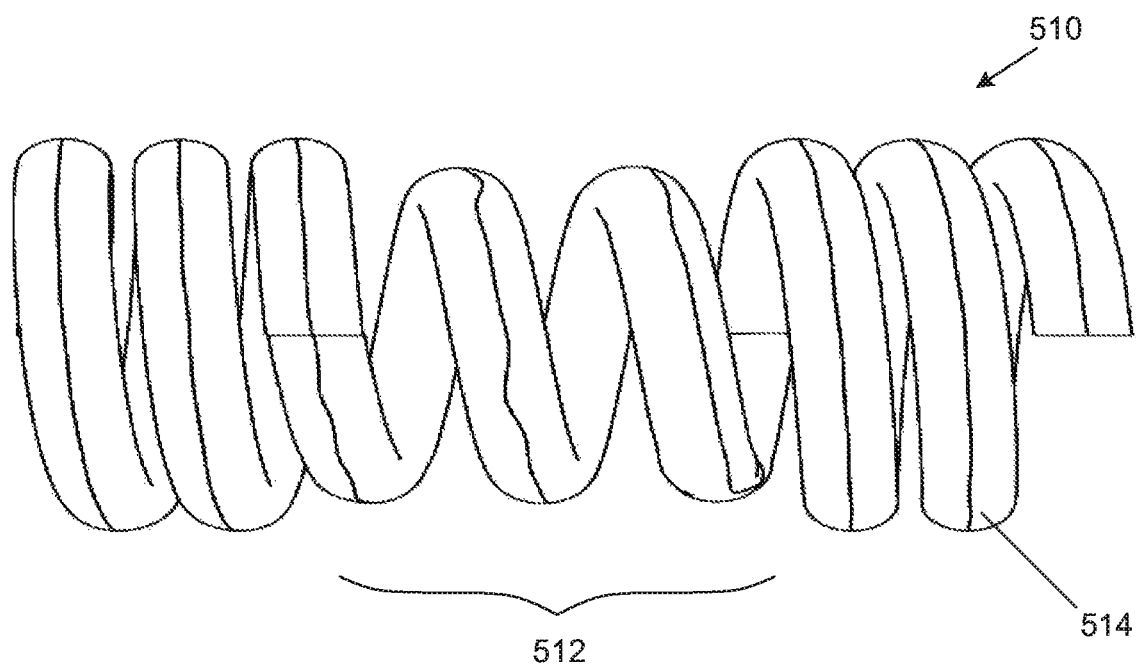
FIG. 28 is a side view of a tube to be used with the frame of FIG. 27, in which the diameter of the spiral varies along the length thereof.
Figure 32A:
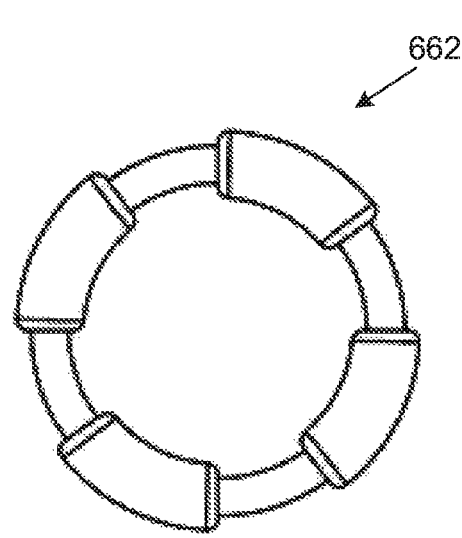
FIGS. 32A and 32B are an end view and three-dimensional view respectively of a further embodiment of a tube for a distender in accordance with the invention, in which the diameter of the tube varies along the length thereof.
Figure 32B:
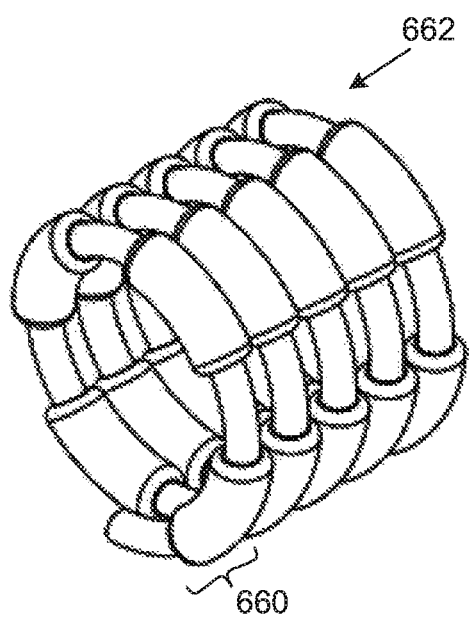

Further, and as illustrated in FIG. 27, the diameter of the frame (500) may be varied along the length of the frame (500). In the embodiment illustrated, a central region (502) of the frame (500) has a smaller diameter than the rest of the frame (500). Due to the tube being threaded through the frame, the variation in frame (500) diameter will occasion a variation in the outer diameter of the tube (510), when expanded, as illustrated in FIG. 28. Similarly to the frame (500), a central region (512) of the spiral (514) formed by the expanded tube (510) has a smaller diameter than the rest of the spiral (514). This will result in the total outer diameter of the distender varying along its length, which may be particularly useful in complex vascular geometries, for example to enable accurate seating and sealing within the Sinus of Valsalva during aortic valvular therapies.

In addition, and as illustrated in FIG. 29, the distender (600) may be shaped so that it assumes a shape having a non-cylindrical cross-section. In the embodiment illustrated, the distender (600) assumes a substantially oval or kidney shape when in the expanded configuration, similarly to the shape of a mitral valve annulus (610) illustrated in FIG. 30. This is useful for seating and sealing within non-circular structures, such as a mitral valve annulus. In order to achieve this, the distender is shape set, either by individually shape setting the tube and frame, or by setting the completed distender upon a specific mandrel.

In accordance with a further embodiment of the invention, and as illustrated in FIGS. 31A and 31B and 32A and 32B, the tube diameter (650, 660) may vary along the length of the tube (652, 662). As illustrated in FIGS. 30 and 31, variation in the tube diameter (650) will cause the tube (652) to have a beaded shape which will enable the tube (652) to fold and expand easier through the frame. In addition, this may enhance perfusion around the tube (652).

Figure 33:
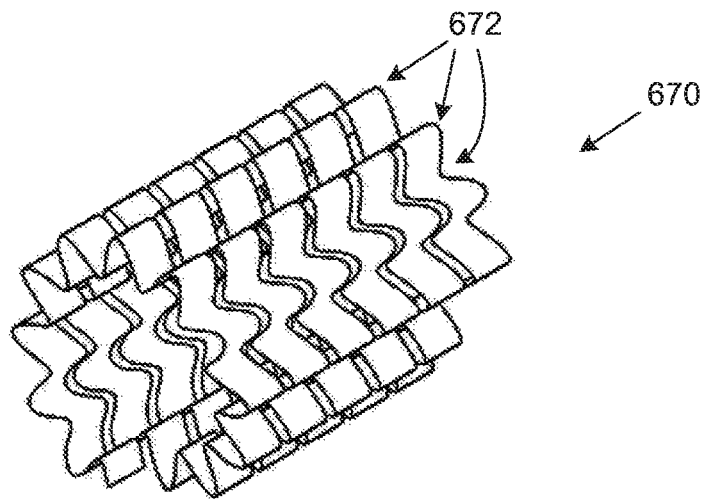
FIG. 33 is a three-dimensional view of yet a further embodiment of a tube for a distender in accordance with the invention, in which the tube has fold lines along the length thereof.

In yet a further embodiment, and as illustrated in FIG. 33, the tube (670) may be provided with fold lines (672) along the length of the tube (670) may create micro-folding during collapsing thereof. This will facilitate better crimping and/or reliable folding of the tube (670) and ultimately minimize the dimensions of the collapsed distender, thereby permitting the device to be navigated to or removed from the operative site.

The distender in accordance with the invention may be manufactured by either threading the tube through the fairly rigid frame or alternatively, by constraining the tube on a mandrel and then using wires to build the frame by braiding the wires through the successive convolutions of the frame. Furthermore, in the event that the frame is manufactured from a synthetic material, such as a polymer, the frame may be manufactured using commonly known forming methods such as dipping or spray moulding, knitting, weaving, welding or the like. Once the tube has been threaded through the frame, or the frame wires braided through the tube, the tube may be heat set to substantially retain its structure through successive expanding and collapsing of the distender. In the case of dip or spray moulding, a frame will be set around the tube encapsulating the distender and thereby resulting in a synthetic frame. This will hold the tube in the desired position.

It will be appreciated that many other non-occlusive dilation and deployment catheter devices exist which fall within the scope of the invention, particularly as regards the shape, configuration and operation thereof. For example, either or both of the frame and the distal end of the catheter may be provided with one or more locator arms which are deployable from a stowed condition to an operative condition in which they are capable of engaging with structures at the operative site. For example, the device may be navigated to a natural heart valve where the locator arms can then be deployed to their operative condition and the device then moved so that the locator arms engage with a heart valve to thereby locate the distender within the heart valve. The locator arms may be curved in the length and flexible with respect to either or both of the frame and catheter. In addition, the locator arms could be hingedly secured to the distender or catheter and may then be deployed through partial expansion of the distender or any other suitable means. Furthermore, the locator arms may be manufactured from the same material as the frame, typically when they are secured to the frame, alternatively the locator arms may be manufactured from an inflatable tube and may be deployed through inflation thereof. Also, in the event of the locator arms are inflatable, they preferably have a varying diameter along their length to facilitate folding thereof during collapsing of the distender.

Also, the device may be provided with one or more pressure sensors on either or both of the catheter and distender. The pressure sensors may then be used to determine whether the device has been navigated correctly to the operative site, for example, by determining a significant drop or increase in pressure when the distender has been navigated into a valve thereby preventing the valve from functioning properly. In this respect, the catheter or distender may also include radio-opaque markers to ensure proper orientation of coronary perfusion elements and/or the correct axial placement of a stented valve or the like.

In addition, the distender may be constructed using one or more tubes to form the spiral. Also, the tube may have more than one inflation point so as to enable faster expansion or collapsing thereof and a smaller profile when in the collapsed configuration. Further, the spiral can be formed by more than one tube and having more than one starting point, thus the individual tubes used do not have to meet.

Even further, the distender may be manufactured to permit attachment and removal thereof from the catheter using any suitable attachment formations, such as a bayonet connection, screw thread or the like.

Figure 34:
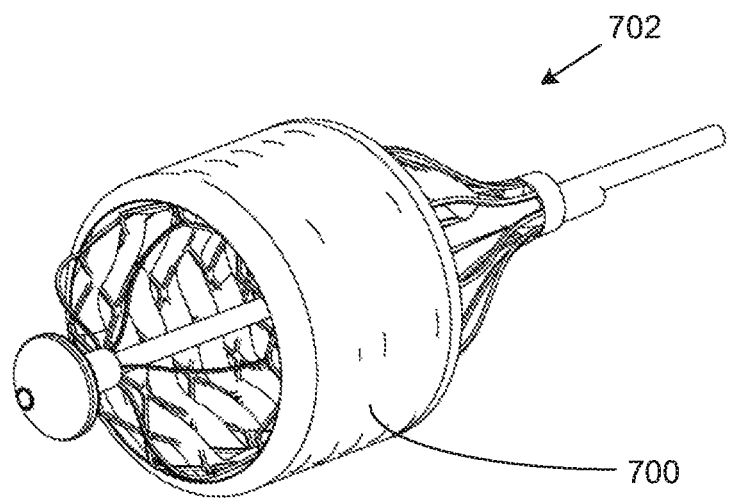
FIG. 34 is a three-dimensional view of a further embodiment of a non-occlusive dilation and deployment catheter device in accordance with the invention, in which an elastic and/or restraining sleeve surrounds the distender.

Also, a thin sleeve (700), preferably manufactured from a perforated elastic material, may surround the distender (702), as illustrated in FIG. 34. In such a case, the sleeve's material may be selected to have a specific elasticity coefficient so that it permits the distender (702) to expand to a specific dimension only, thereby preventing over-expansion of the distender (702). In addition, the sleeve may further facilitate collapsing of the distender by imparting a radial force thereon.

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure. It will be appreciated that different combinations of the features of the various described embodiments may be used.

The invention claimed is:

1. A non-occlusive dilation distender movable between a collapsed configuration which enables introduction and removal thereof to and from an operative site in a vessel or other hollow organ of a patient, and an expanded configuration in which the distender assumes a radially expanded condition and defines a flow path therethrough,
   wherein the distender includes a substantially tubular, radially expandable frame having a plurality of radially spaced apertures about the frame and at least one inflatable tube threaded through at least some of the radially spaced apertures with the tube shaped to extend in a spiral when inflated, wherein the frame maintains the spiral shape of the inflatable tube when inflated by preventing relative movement between adjacent convolutions of the spiral shaped tube along the length of the distender to thereby increase the distender's ability to resist radial and axial loading,
   and wherein the distender is movable to the expanded configuration by inflating the tube, and from the expanded configuration to the collapsed configuration by deflating the tube.

2. The distender as claimed in claim 1, wherein the frame has a mesh-like configuration with the tube being threaded through the mesh along a generally spiral path.

3. The distender as claimed in claim 1, wherein the diameter of the frame varies along its length to permit variation in the outer diameter of the distender along its length in the expanded configuration.

4. The distender as claimed in claim 1, wherein the frame and tube are shaped so that the distender assumes a shape having a non-cylindrical cross-section when in the expanded configuration.

5. The distender as claimed in claim 1, wherein a valve is provided within the flow path to permit flow of blood through the flow path predominantly in one direction.

6. The distender as claimed in claim 1, wherein the tube diameter varies along the length thereof.

7. The distender as claimed in claim 1, wherein the tube is provided with fold lines along its length to facilitate collapsing of the distender.

8. The distender as claimed in claim 1, wherein a stent is pre-crimped over the distender when in a collapsed configuration.

9. The distender as claimed in claim 1, wherein the frame is manufactured from one of the group consisting of a laser cut tube; a sleeve of elastomeric material; a plurality of braided wires; and a plurality of bonded wires or ribbons.

10. The distender as claimed in claim 1, wherein the apertures of the frame are spaced to permit the pitch of successive convolutions of the spiral along the length of the frame to be varied.

11. The distender as claimed in claim 1, wherein a sleeve manufactured from a perforated elastic material, surrounds the distender.

12. The distender as claimed in claim 1, wherein the frame is manufactured from a shape memory alloy with a pre-set diameter so as to assist in expanding or collapsing the distender.

13. A non-occlusive dilation and deployment catheter device which includes:
   a catheter having a distal end configured for entering a patient and a proximal end for manipulating the device, the device including a distender as claimed in claim 1 at or near the distal end of the catheter.

14. The catheter device as claimed in claim 13, wherein the catheter includes an internal member and an external member with the distal end of the frame being attached to the distal end of the internal member and the proximal end of the frame being attached to the distal end of the external member so as to enable the frame to be placed under tension or compression through relative lengthwise movement of the distal ends of the internal member and external member.

15. The catheter device as claimed in claim 13, wherein the catheter includes at least one biasing member that is attached to one or both of the distal end and the proximal end of the frame and which is configured to exert one or both of an axial force and a torsional force on the frame to place the frame under tension or compression.

16. The catheter device as claimed in claim 15, wherein the biasing member is further configured to exert a torsional force on the frame.

17. The catheter device as claimed in claim 15, wherein the biasing member is integral with the frame.

18. The catheter device as claimed in claim 13, wherein the distender is held in a retractable sheath in the collapsed configuration.

19. The catheter device as claimed in claim 13, wherein one or more pressure sensors are provided on either or both of the catheter and distender.

20. The catheter device as claimed in claim 13, wherein one or more locator arms are secured to either or both of the frame and the distal end of the catheter and which are deployable from a stowed condition to an operative condition in which they are able to engage with structures at the operative site.

* * * * *